United States Patent [19]
Loree et al.

[11] Patent Number: 5,894,340
[45] Date of Patent: Apr. 13, 1999

[54] METHOD FOR QUANTIFYING OPTICAL PROPERTIES OF THE HUMAN LENS

[75] Inventors: Thomas R. Loree, deceased, late of Albuquerque, by Bliss Kelly-Loree, personal representative; Irving J. Bigio, Los Alamos, both of N.M.; Joseph A. Zuclich, San Antonio, Tex.; Tsutomu Shimada, Los Alamos, N.M.; Karlheinz Strobl, Fiskdale, Mass.

[73] Assignee: The Regents of the University of California, Los Alamos, N.M.

[*] Notice: This patent issued on a continued prosecution application filed under 37 CFR 1.53(d), and is subject to the twenty year patent term provisions of 35 U.S.C. 154(a)(2).

[21] Appl. No.: 08/744,678

[22] Filed: Nov. 6, 1996

Related U.S. Application Data

[63] Continuation of application No. 08/390,019, Feb. 17, 1995, abandoned.

[51] Int. Cl.$^6$ ........................................................ A61B 3/00
[52] U.S. Cl. ........................... 351/246; 351/205; 351/221
[58] Field of Search ........................... 351/200, 205, 351/221, 246; 356/318; 128/665

[56] References Cited

U.S. PATENT DOCUMENTS 5,303,026  4/1994  Strobl et al. ..................... 356/318
5,369,496  11/1994  Alfano et al. ..................... 128/446

OTHER PUBLICATIONS

Joseph A. Zuclich et al., "Rapid Noninvasive Optical Characterization of the Human Lens," Lasers in the Life Sciences 6(1), 39 (1994).

*Primary Examiner*—Huy Mai
*Attorney, Agent, or Firm*—Samuel M. Freund

[57] ABSTRACT

Method for quantifying optical properties of the human lens. The present invention includes the application of fiberoptic, OMA-based instrumentation as an in vivo diagnostic tool for the human ocular lens. Rapid, noninvasive and comprehensive assessment of the optical characteristics of a lens using very modest levels of exciting light are described. Typically, the backscatter and fluorescence spectra (from about 300- to 900-nm) elicited by each of several exciting wavelengths (from about 300- to 600-nm) are collected within a few seconds. The resulting optical signature of individual lenses is then used to assess the overall optical quality of the lens by comparing the results with a database of similar measurements obtained from a reference set of normal human lenses having various ages. Several metrics have been identified which gauge the optical quality of a given lens relative to the norm for the subject's chronological age. These metrics may also serve to document accelerated optical aging and/or as early indicators of cataract or other disease processes.

7 Claims, 8 Drawing Sheets

METHOD FOR QUANTIFYING OPTICAL PROPERTIES OF THE HUMAN LENS

This application is a continuation of U.S. patent application Ser. No. 08/390,019 filed on Feb. 17, 1995, now abandoned.

This invention was made with government support under Contract No. W-7405-ENG-36 between the U.S. Department of Energy and the Regents of the University of California. The government has certain rights in the invention.

FIELD OF THE INVENTION

The present invention relates generally to the evaluation of the characteristics of the human ocular lens and, more particularly, to the collection of backscatter and fluorescence spectra resulting from excitation using modest levels of electromagnetic excitation of a lens under investigation in the region between 300- and 600-nm in order to determine the optical signature thereof and assess the state of health of the lens.

BACKGROUND OF THE INVENTION

Age-related changes in lens properties are due partially to the very gradual growth of the lens and partially to the cumulative photochemical consequences of ambient exposure to the near-ultraviolet and blue wavelengths absorbed by the lens. It is not uncommon to find that lens aging processes have progressed to the extent where vision is significantly degraded, while other ocular tissues have yet to exhibit noticeable degenerative effects. Because lens tissue never sheds any of its cells, the photoproducts induced by ambient light exposures accumulate within the lens. As a result, the near-uv absorption observed in the young lens begins to impinge upon the short, visible spectrum so that there is a gradual attenuation of blue light in the aging lens, and the initially clear lens takes on an increasingly yellowish and ultimately brunescent coloration.

Concomitant with the age-related changes in lens absorption and scattering is a corresponding evolution of the lens autofluorescence. The fluorescence from lens photoproducts, being close molecular derivatives of the near-uv absorbing, blue-fluorescing chromophore found in the young lens, becomes stronger and encompasses longer visible wavelengths in the aging lens. In the aged lens (>80 yr), a bright ambient environment (normal sunlight) can induce a fluorescence glare of sufficient intensity to impair visual function.

Although the etiology of cataract formation is still under investigation, there is a general consensus that photochemically induced changes in lens molecular composition ultimately result in cataract expression. This engenders further changes in the visible light absorption, scattering and fluorescent properties of the aging lens. Numerous investigations have examined the age-related and cataract-associated optical changes as means for monitoring signs of premature aging or early indication of cataract. In addition, diseases including diabetes and use of photosensitizing drugs may precipitate relatively rapid cataract formation, and characteristic changes in the optical properties of the lens which presage this consequence have been reported.

Various experimental approaches to characterizing the optical qualities of the lens have been reported. Some are noninvasive and possibly suitable for in vivo measurements in the alert human patient. Others are too time-consuming and tedious for use with alert subjects. Yet others require the exposure of the subject to undesirable levels of near-UV and visible radiation. Often, existing approaches, while measuring specific aspects of the lens spectral properties, do not give a sufficiently complete optical profile to be of value in assessing the overall impact of aging, in tracking progress towards eventual cataract formation, or in discerning the effects on the lens of other diseases or of various photosensitizing drugs.

Accordingly, an object of the present invention is to provide a rapid, noninvasive and safe method for collecting extensive quantitative optical data from human lenses in order to discern departures from normalcy.

Additional objects, advantages and novel features of the invention will be set forth in part in the description which follows, and in part will become apparent to those skilled in the art upon examination of the following or may be learned by practice of the invention. The objects and advantages of the invention may be realized and attained by means of the instrumentalities and combinations particularly pointed out in the appended claims.

SUMMARY OF THE INVENTION

To achieve the foregoing and other objects, and in accordance with the purposes of the present invention, as embodied and broadly described herein, the method for determining the optical quality of human ocular lenses of this invention includes the steps of: illuminating the lens under investigation with one or more chosen wavelengths of electromagnetic exciting radiation; measuring the intensity of the exciting radiation; collecting backscattered and fluorescent radiation from the lens excited thereby; and normalizing the collected backscattered and fluorescent radiation to the measured intensity of the exciting radiation.

Preferably, the illuminating wavelength is swept through a chosen range of wavelengths.

It is preferred that the collected backscattered and fluorescent radiation be compared with data from similar measurements obtained from numerous normal human lenses from various age groups; whereby the optical quality of the lens under investigation can be determined relative thereto.

Preferably also, the chosen range of excitation wavelengths is between 300- and 600-nm, and the range of collected wavelengths is 300- to 900-nm.

Benefits and advantages of the present invention include the ability to collect extensive quantitative data from individual lenses in vivo for the purpose of observing changes therein, rapidly, safely, economically, and noninvasively.

BRIEF DESCRIPTION OF THE DRAWINGS

The accompanying drawings, which are incorporated in and form a part of the specification, illustrate the embodiments of the present invention and, together with the description, serve to explain the principles of the invention. In the drawings.

DETAILED DESCRIPTION

Briefly, the present invention includes the application of fiberoptic, OMA-based instrumentation as an in vivo diagnostic tool for the human ocular lens. The instrumentation allows rapid, noninvasive, comprehensive assessment of the optical characteristics of a lens while using very modest levels of exciting light. Typically, the backscatter and fluorescence spectra (from approximately 300- to 900-nm) elicited by each of several exciting wavelengths (from approximately 300- to 600-nm) can be collected within a few seconds. The resulting optical signature of individual lenses is then used to assess the overall optical quality of the lens. Several metrics have been identified which gauge the optical quality of a given lens relative to the norm for the subject's chronological age. These metrics may also serve to document accelerated optical aging and/or as early indicators of cataract formation or other disease processes.

Figure 1:
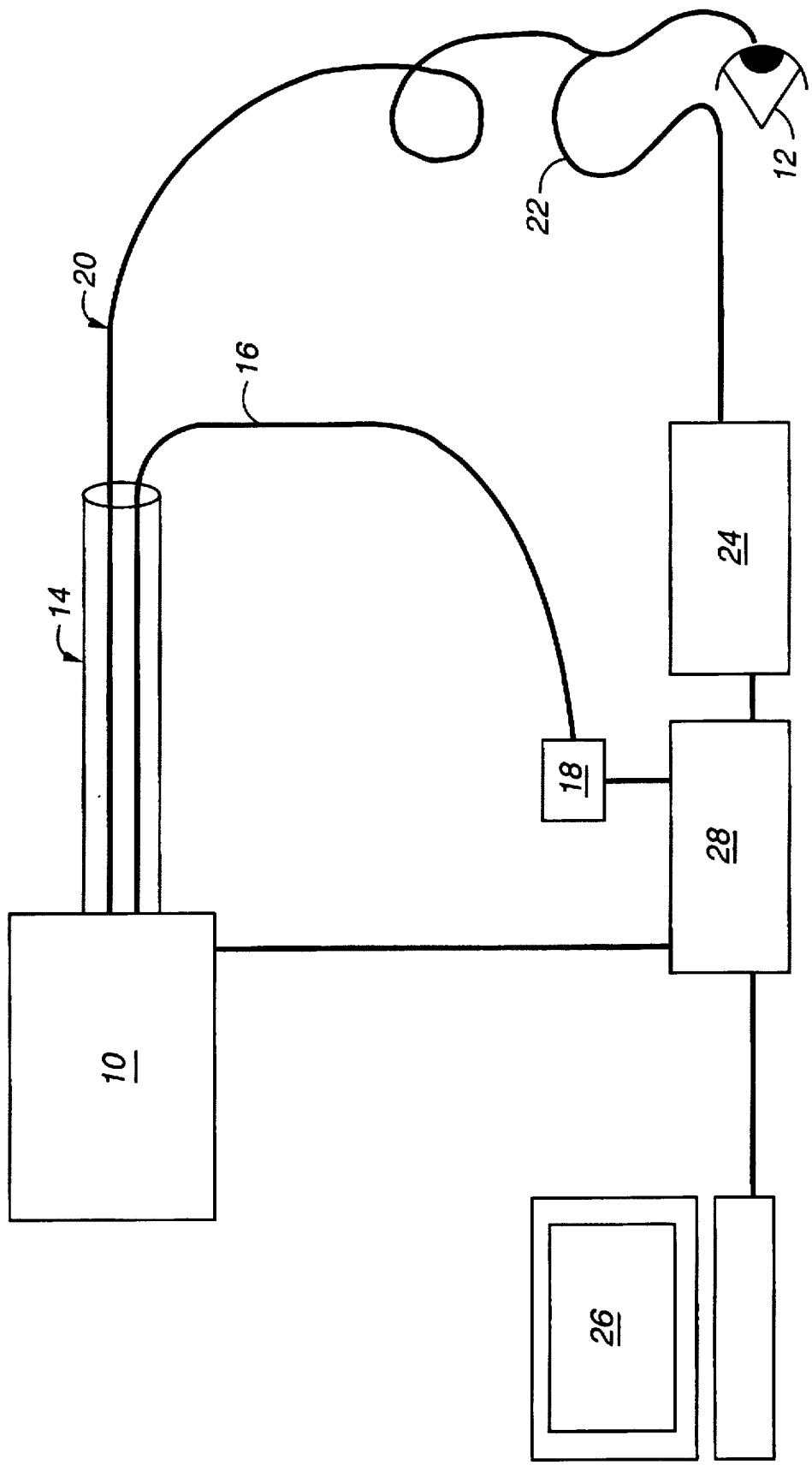
FIG. 1 is a schematic representation of an apparatus used to practice the method of the present claimed invention.

Turning now to the drawings, FIG. 1 is a schematic representation of the apparatus employed to practice the method of the present invention. A similar apparatus was initially employed for discrimination of cancerous versus normal tissues based on the measured scattering and fluorescence profiles of the tissue samples. See, e.g., Karlheinz Strobl et al., "Apparatus and Method for Spectroscopic Analysis of Scattering Media," U.S. Pat. No. 5,303,026, which issued on Apr. 12, 1994. Depending on the specific target, any of several laser sources can be utilized to select wavelengths best suited for characterizing the optical features of cancerous or otherwise abnormal tissue. Minor modifications to the hardware and software were made for the application of the system to the optical profiling of the ocular lens. In this instance, illumination using many uv and visible exciting wavelengths was desirable, so an arc lamp source was incorporated into the apparatus.

Light source, 10, includes a 300 W xenon arc lamp with its output directed through a grating monochromator with slits chosen to select a bandwidth of about 10-nm (full-width-at-half-height) and through an optical shutter for selection of a chosen pulse width and repetition rate. The wavelength-selected arc lamp radiation was collected and delivered to the lens to be investigated, 12, using fiberoptic bundle, 14. At the input end, the fiberoptic bundle consisted of a parallel array of seven fibers. The central fiber, 16, of this array (600 μm diameter) delivered a portion of the exciting light to photodiode, 18, which was used to create a normalization channel against which to reference the intensities of scattered and emitted (fluorescence) light from the targeted tissue. The remaining six fibers, 20, (all 200 μm diameter) delivered the exciting radiation to the lens. At the target end, delivery fibers, 20, were arranged in a tight-packed circular array surrounding a single, 200 μm collection fiber, 22. The collection fiber delivered the backscatter and fluorescence responses from the lens to an imaging spectrograph, 24. The spectrum thus created by each pulse of exciting light is collected by a 1024-element intensified silicon photodiode array detector interfaced to an optical multichannel analyzer (OMA). Only 700 channels of the OMA were utilized to record the spectral reply from the lens over the wavelength range from about 275- to 931-nm. High spectral resolution is not required when dealing with the broad absorption and emission bands associated with biological tissues. Therefore, the sensitivity (signal/noise ratio) of the OMA spectrometer system was improved by combining channel counts (four channels into one bin) to yield 175 spectral bands over the indicated wavelength range. The voltage output from photodiode, 18, was applied to the 176th OMA bin as the normalization channel. Thus, the data set generated by each exciting pulse consisted of 176 bin counts, the first 175 of which mapped the spectral reply from the sample, while the 176th provided the correction for intensity variations in the source (arc lamp/monochromator combination) and/or for variation in the duration of the exciting pulse. Data acquisition and analysis system, 26, controls and interacts with the data generating and gathering apparatus through control electronics module, 28.

The protocol followed with each lens was first to adjust the monochromator to its white light throughput setting and collect the backscatter spectrum associated with a white-light excitation pulse. Then the monochromator was typically adjusted to 600-nm output and stepped down in wavelength at 10-nm increments to 300-nm. Thus, 31 spectra were collected, each showing the backscatter elicited by a particular exciting wavelength, as well as any induced fluorescence. The exciting wavelength was selected by a stepper motor attached to the monochromator. Both the stepper motor and the shutter controlling the duration and frequency of the exciting light pulses were computer controlled by data acquisition system, 26, so that an initialization command triggered the automated collection of the 31 backscatter/fuorescence spectra or another programmed sequence of spectra. As each spectrum was collected, it was transferred and stored in computer memory. The software employed controlled the exposure duration by repeatedly sampling the strength of the reply from the target lens. This procedure allowed the optimization of the system signal-to-noise ratio by minimizing data collection time while avoiding saturation of the OMA detector (and thereby avoiding loss of quantitative information) in any of the bins.

Depending on the strength of the reply from individual lens samples, collection of the automated sequence of backscatter/fluorescence spectra could be completed in 1–10 seconds; typically 3 seconds. The white-light backscatter spectrum was generally collected with a minimal exposure time (~10 ms). The white-light power delivered through the fiber array to the lens was measured to be about 1 mW. The peak power levels at individual wavelengths delivered to a lens ranged from 1.8 to 5.2 μW. Human ocular lens exposures at the power levels employed in the demonstration of the present invention are within published safety standards for monochromatic (laser) and broad-band sources, unless exposure durations far in excess of those required to complete the lens optical characterization measurements are utilized.

The results described hereinbelow were obtained using extracted human lenses. Whole encapsulated lenses were harvested by several participating eye banks, placed in buffered saline solution and refrigerated. Data was collected at between 1 and 7 days post-mortem. However, many samples began to show signs of deterioration (sloughing off of surface layers into solution) and were not usable beyond 4–5 days post-mortem.

Cataractous lens samples (nuclei) were obtained following extracapsular cataract surgery and handled and measured in the same way as the normal lenses. The source of cataractous lenses for the preliminary experiments did not provide clinical descriptions of the opacities and no discriminatory measurements by grade or type of cataract were attempted.

The lenses were placed in a cell designed to provide an optical surrounding consistent with the in situ lenses. That is, lenses were supported by disks of black plastic (representing the iris) having fixed pupillary apertures. Generally, a disk having a 7 mm aperture was used and found to provide sufficient support for the lens to rest over the aperture without slippage. The lens-supporting disks rested on a shelf carved into a hemispheric cup (also black plastic) having a 1.5-cm inner diameter such that the inner surface of the hemisphere was at the appropriate distance from the lens to represent the pigmented retina. Both the vitreous and aqueous humor were represented by saline solution which filled the hemispheric cup and also covered the lens to a depth of $\geq 3$ mm (representing the correct thickness for the aqueous humor). The exciting light was directed through the aperture of the lens-supporting disk. The tip of the fiber-optic delivery/collection array was placed in contact with the saline solution in order to avoid an intense backscatter/reflection from the air-fluid interface.

Initially, measurements were carried out with the fiber bundle tip placed at various distances from the lens surface (from 0 to 6 mm). Although the absolute intensity of the backscatter/fluorescence response from the lenses dropped rapidly with distance, the measurements demonstrated that the relative features within a set of spectra were independent of distance between the fiber bundle tip and the lens (and thus not distorted by geometrical factors). It would then be apparent to a skilled artisan after studying the present disclosure that the method of the present invention could be implemented in vivo with the fiber bundle tip incorporated into a flat-faced contact lens positioned on the eye during the programmed sequence of exposures. Minor variations between individuals in the distance from fiber tip to the lens surface should not affect the backscatter/fluorescence measures of interest.

Having generally described the present invention, the following Examples are presented to more particularly illustrate its teachings.

EXAMPLE 1

Figure 2:
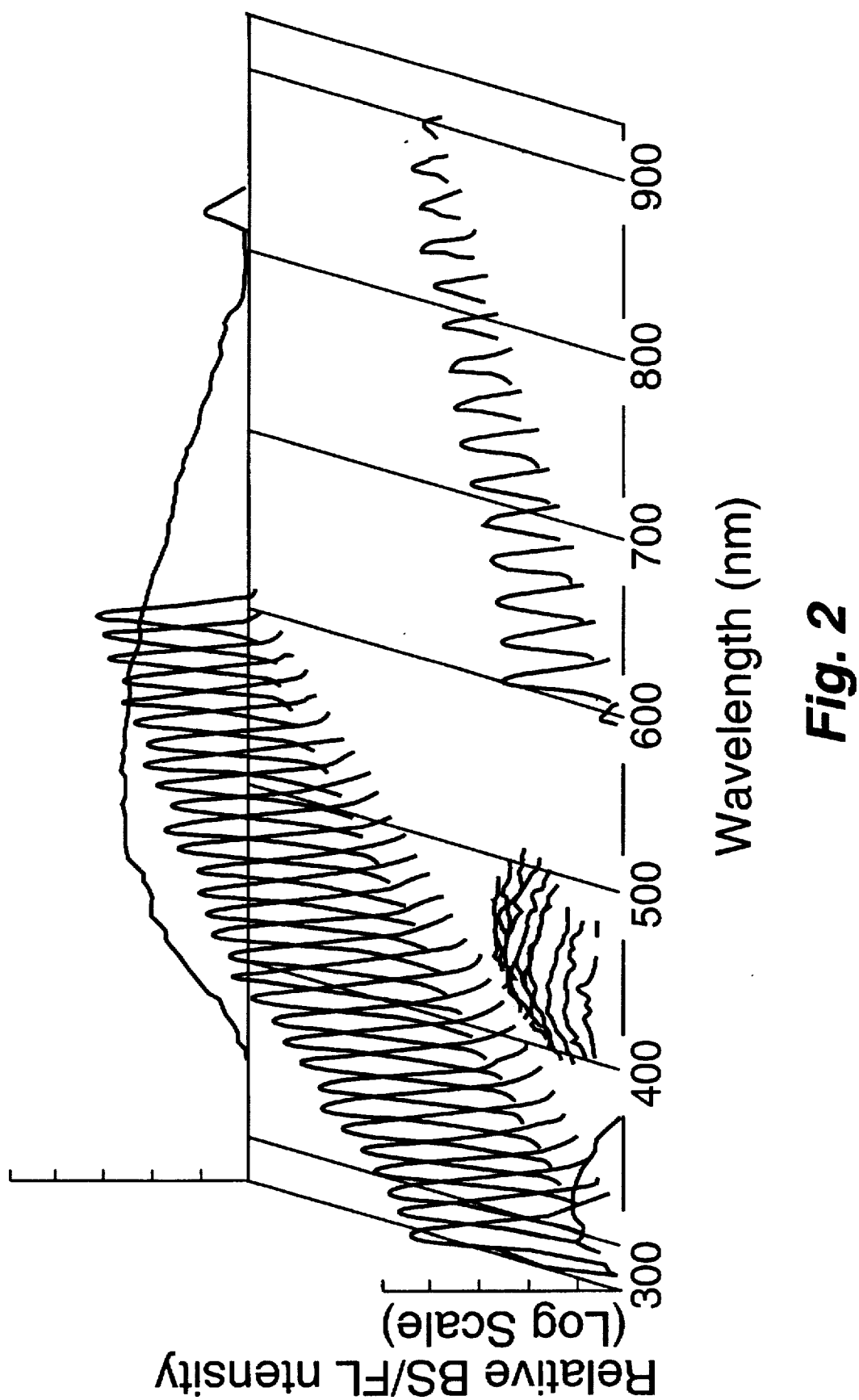
FIG. 2 shows a sequence of backscatter/fluorescence spectra collected from a young lens.
Figure 3:
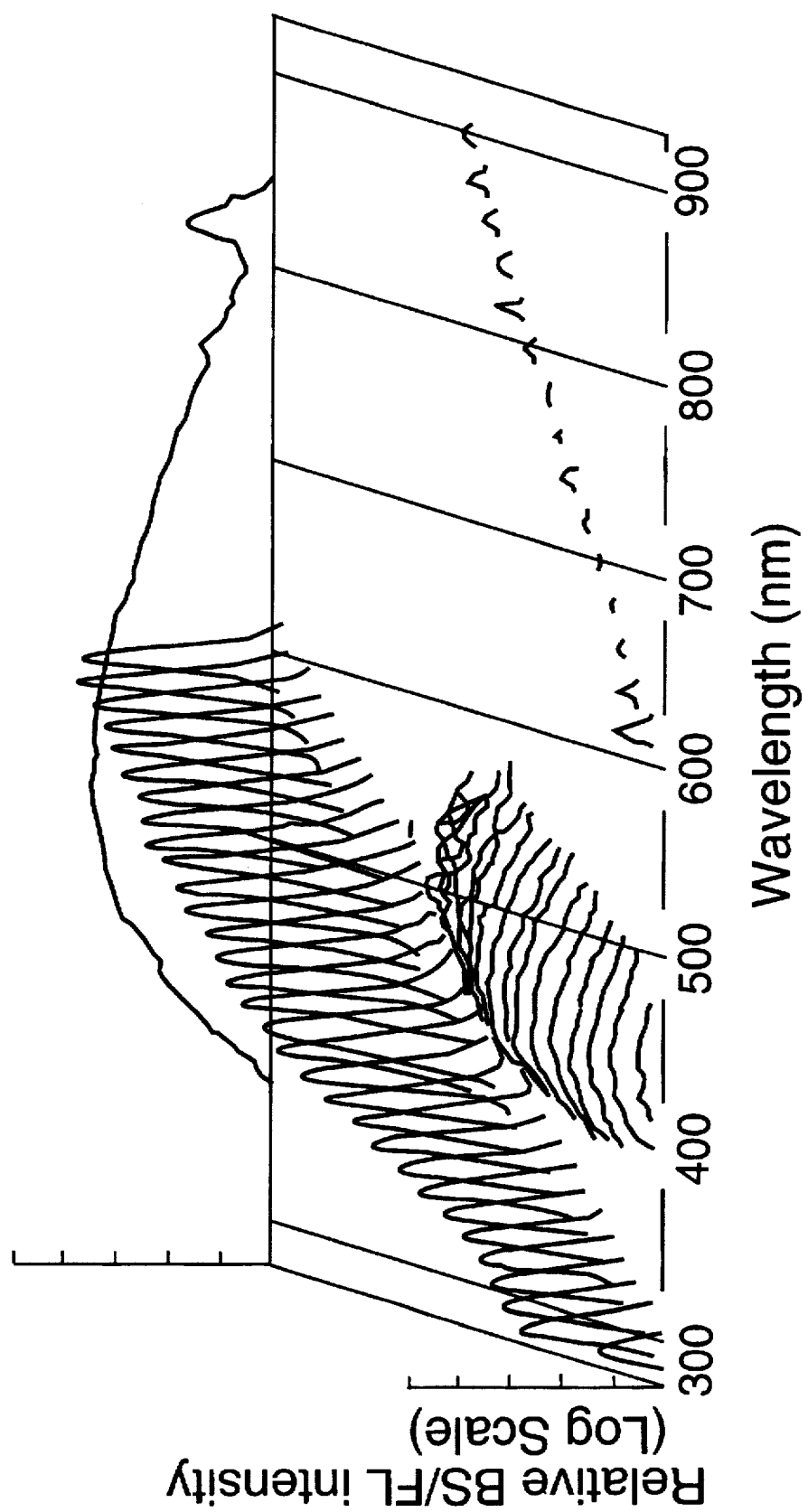
FIG. 3 shows a sequence of backscatter/fluorescence spectra collected from an old lens.

FIGS. 2 and 3 depict typical sequences of 32 backscatter/fluorescence spectra collected from relatively young (38 yr) and old (87 yr) lenses, respectively. The backscatter/fluorescence intensity (bin count) is plotted on a log scale as a function of wavelength. Reading from the bottom-left of each figure, curves 1 through 31 depict the backscatter (relatively narrow peaks centered at the exciting wavelength) and fluorescence (broad peaks primarily in the 400–550-nm range) elicited by 300-, 310-, . . . 600-nm excitation, respectively. Each spectrum has been divided by its respective normalization channel so that features within each sequence of curves can be quantitatively compared. The 32nd and uppermost curve in each figure depicts the full-spectrum backscatter resulting from white-light excitation.

With the lens from the 38 yr old subject (FIG. 2), it is seen that no measurable fluorescence is induced by excitation wavelengths $\geq 400$-nm and that the fluorescence induced at shorter wavelengths is weak relative to the corresponding backscatter intensities. For the older lens (FIG. 3), not only do longer exciting wavelengths (up to about 500 nm) elicit measurable fluorescence, but the fluorescence bands are generally broader and considerably more intense relative to the corresponding backscatter intensities. It has been generally found that the backscatter and fluorescence intensities for all exciting wavelengths tend to increase with age. Therefore, the relative changes within sequences of backscatter/fluorescence curves form the basis for the following analyses.

Figure 4:
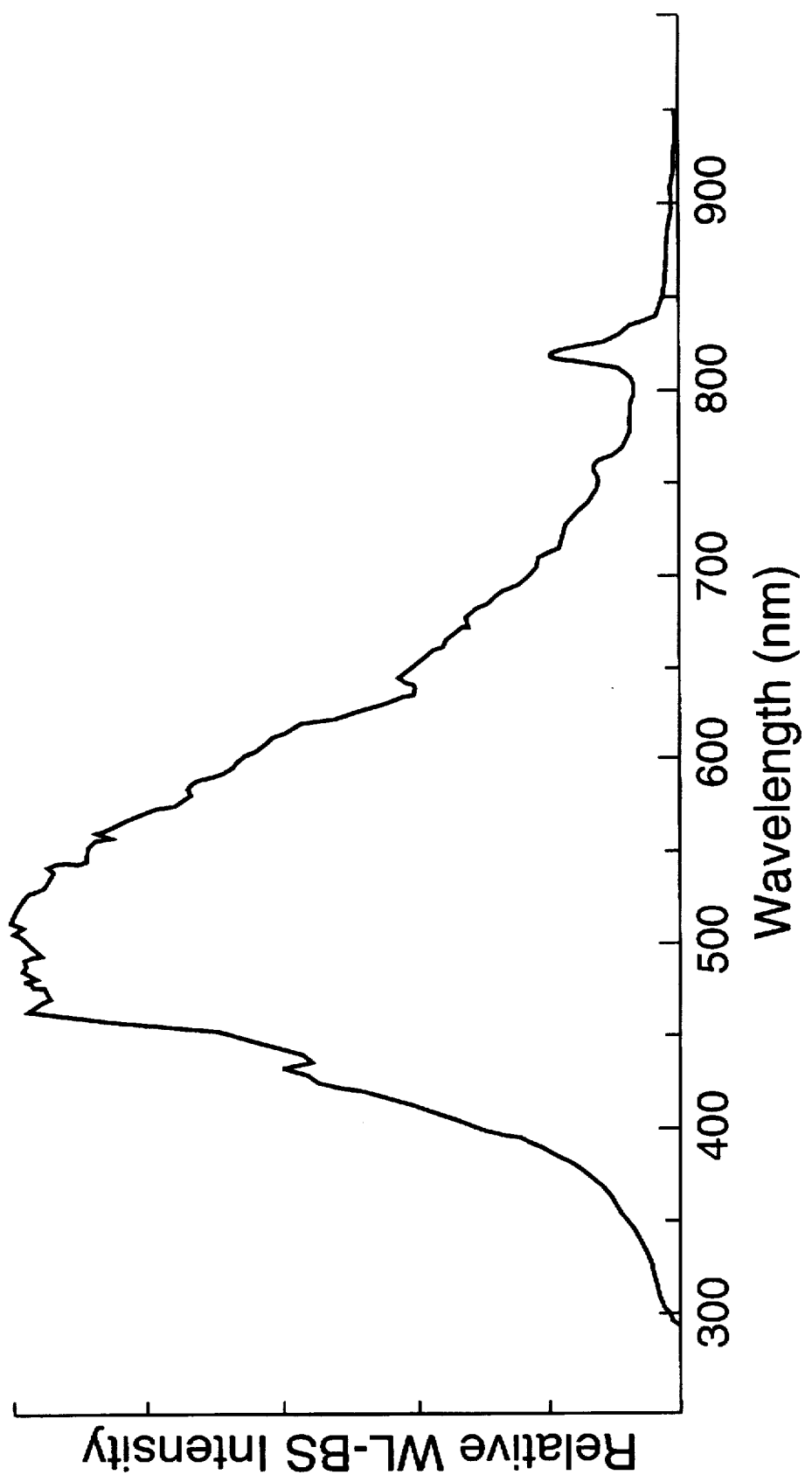
FIG. 4 shows the backscatter spectrum generated from a young lens excited with white light.
Figure 5:
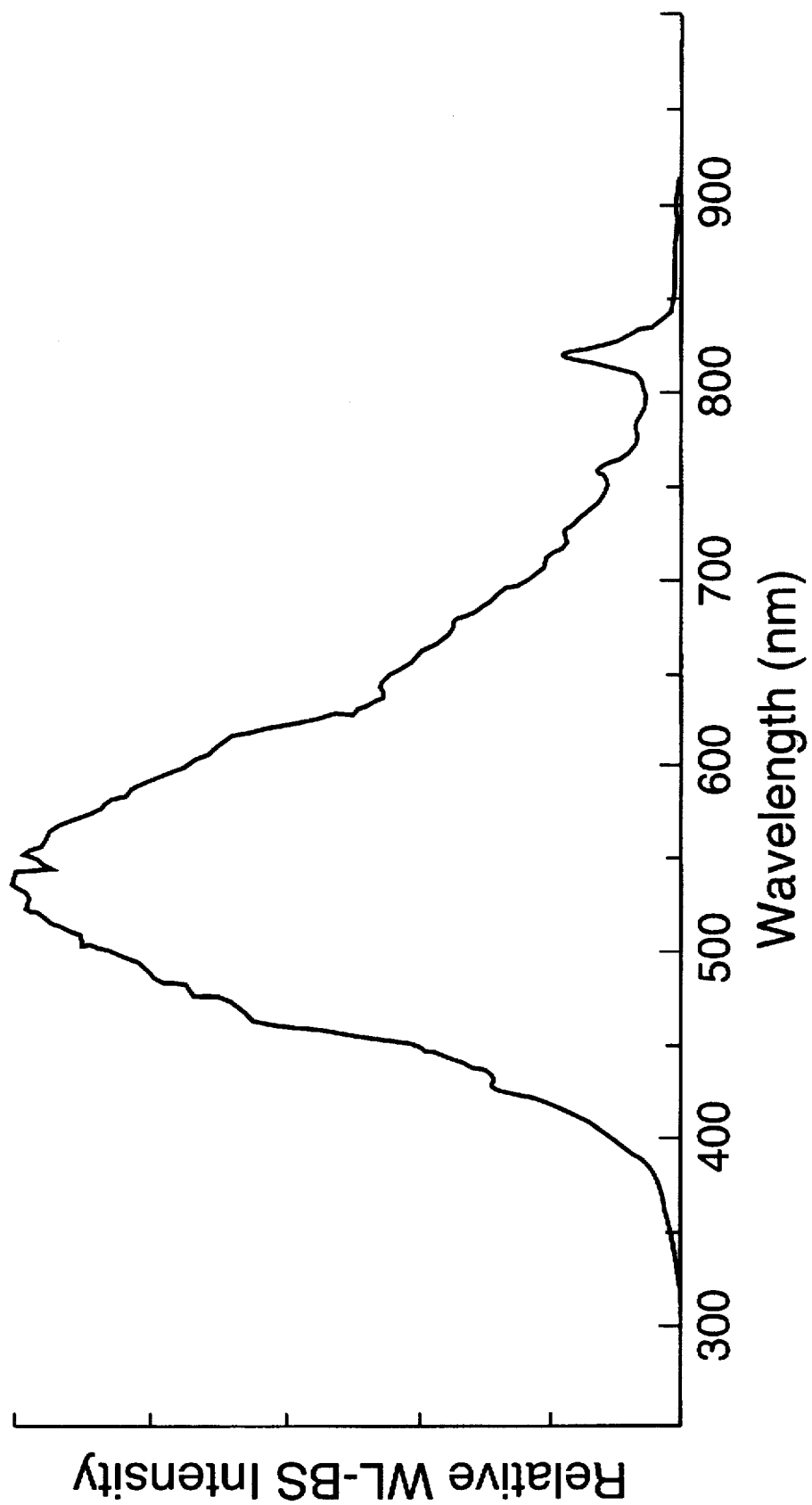
FIG. 5 shows the backscatter spectrum generated from an old lens excited with white light.
Figure 6:
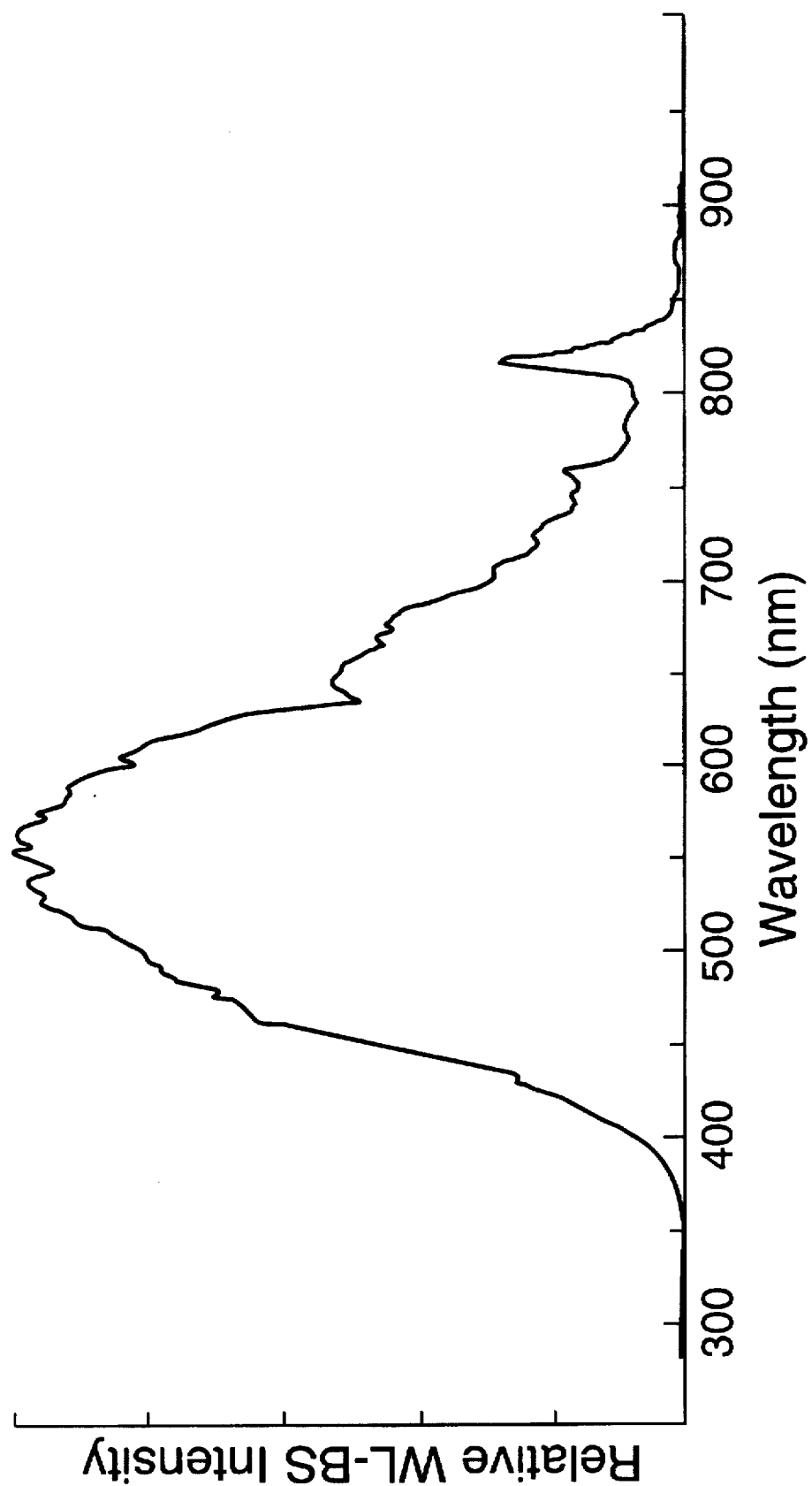
FIG. 6 shows the backscatter spectrum generated from a cataractous lens excited with white light.

FIGS. 4–6 illustrate typical white-light backscatter (WL-BS) spectra for young, old (but noncataractous), and cataractous lenses, respectively. In FIGS. 4–6, the backscatter intensities are plotted on linear scales. The young lens as shown in FIG. 4 (this is the WL-BS curve abstracted from the optical profile of the 38 yr old subject depicted in FIG. 2) tends to have a more pronounced backscatter at shorter wavelengths rising to a maximum intensity at about 450 nm. The aged lens (FIG. 5 and the same 87 yr. old lens shown in FIG. 3) has a WL-BS much more heavily weighted to the red and peaking at approximately 550-nm. Each of eleven cataractous lenses examined, with subject ages ranging from 65 to 88 yrs., had features typified by FIG. 6 (from a 73 yr. old subject). There is a great similarity between the WL-BS curves for cataractous and noncataractous lenses of comparable ages, but the shoulder centered at about 650-nm seems consistently more pronounced in spectra is from the cataractous lenses. The relatively steep drop spanning the 620–640-nm range in the WL-BS curve just preceding the 650-nm shoulder also is consistently more pronounced with the cataractous lenses.

EXAMPLE 2

The method of the present invention allows a comprehensive assessment of the optical characteristics of the human lens in a short time and with low levels of exciting light. By examining the three-dimensional spectral profile (normalized scattered/emitted intensity versus emitted wavelength as a function of exciting wavelength) for a population of approximately 100 lenses, numerous optical metrics have been identified which gauge the optical quality of a given lens relative to the norm for the subject's chronological age. Additionally, parameters which serve as measures of accelerated optical aging and/or as early indicators of cataract or other disease processes have been identified.

Since there are likely to be many complicating factors in measuring absolute values of scattering and fluorescence in vivo in alert subjects, it is believed that the most useful metrics will be those which normalize optical characteristics which develop with age and environmental insult to innate and relatively stable optical parameters in the same lens. Thus, for example, one may monitor the fluorescence induced by short visible wavelengths (absent in the young lens) relative to that induced by uv absorption (present at all ages and with a relatively minor progression with age). Similarly, the young normal lens will exhibit minimal scattering of visible wavelengths relative to that for uv wavelengths where the lens is optically dense. Therefore, important metrics to follow are the ratios of blue, green, and red backscattering to uv backscattering, since these ratios are expected to progress with age and show the cumulative consequences of ambient or above-ambient light exposures.

As an example of a metric which demonstrates a specific trend with age, the ratio of the fluorescence (FL) induced by 420-nm to that induced in the same lens by 360-nm excitation (420/360 FL ratio) was arbitrarily chosen. The latter wavelength corresponds to the near-uv absorption peak of the primate lens and is an efficient wavelength for inducing a strong fluorescence in lenses of all ages. By contrast, no measurable fluorescence is induced in the young lens by wavelengths as long as 420-nm. In general, the 420-nm induced fluorescence strength in lenses from subjects $\leq$40 yr old could not be quantitated, so that the 420/360 FL ratio is a useful metric only for ages $\geq$40. There is a generally increasing trend of the 420/360 FL ratio with age, but sufficient fluctuation exists to make definition of a best-fit curve problematical. Therefore, an attempt to define a baseline curve for this metric as a function of age was made. This definition required winnowing out those lenses whose fluorescence ratios deviated from the normal age progression either because of innate sensitivity to ambient light exposures or due to any of a variety of environmental or systemic insults (e.g., extraordinary light level exposures, microwave or other radiation insult, diseases such as diabetes or incursion by any of a variety of photosensitizing chemicals or drugs, which can affect the optical quality of the lens). The winnowing process was accomplished by first identifying all cases where one or both of a pair of "normal" lenses had a significantly higher 420/360 FL ratio than the prevailing age trend suggested by the data base. For each of those cases, other optical properties which generally exhibited a definitive progression with age were examined. These metrics included the ratio of backscatter intensity with a red exciting wavelength to that with uv excitation (600/360 backscattering (BS) ratio) and the wavelengths of the initial rise and the peak of the WL-BS curve (which becomes progressively more red-shifted with age).

A near 100% correlation across all of the indicators for those lenses which exhibited a significant deviation from the norm for their chronological age was observed. In every case (about 20 lenses) where a lens exhibited a 420/360 FL ratio significantly above the prevailing age trend fine, a higher 600/360 backscattering ratio and a more red-shifted WL-BS curve than would be expected for lenses of the corresponding ages were also found. Since the optical quality of these lenses has obviously been impacted by some adverse circumstances which resulted in an apparently accelerated optical aging, these lenses were deleted from the plots of the optical metrics as a function of age. The results are set forth in FIG. 7, which depicts the baseline age trend curve (solid line) derived as a best fit to the edited data (hollow data points). Extrapolating the best-fit curve to lower ages, it may be observed that the solid line comes very close to passing through the chronological origin.

Figure 7:
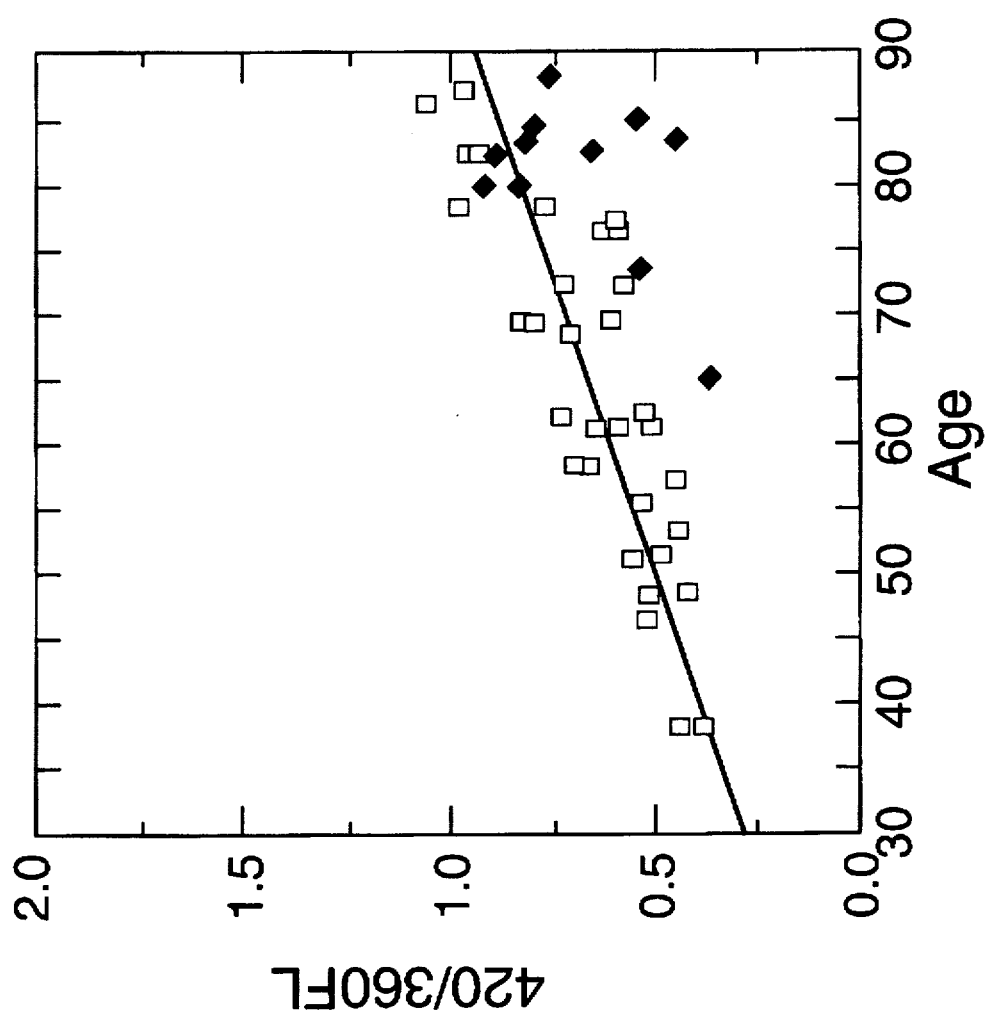
FIG. 7 shows the ratio of the fluorescence peak intensity induced by 429-nm excitation to the fuorescence peak intensity induced by 360-nm excitation as a function of age. The solid line represents the best fit to the normal (open symbol) lens data. The solid symbols are the corresponding 420/360FL ratios obtained for cataractous lenses.

Also plotted on FIG. 7 are the 420/360 FL ratios for eleven cataractous lenses (filled data points). It is seen that the cataractous lenses generally counter the trend of increasing 420/360 FL ratio with age. This is understood by considering that with the formation of a discrete opacity, the absorption and scattering of the 420-nm radiation (or of any other visible wavelength) is increased even beyond the levels implied by the chronological aging of the lens, so that fewer of the incident photons are able to penetrate the tissue to specifically excite the fluorescing chromophore(s). It is believed by the inventors that ambient light exposures and other aggravating factors drive the lens up an age "ramp" either at the baseline rate indicated by the solid line of FIG. 7 or at an accelerated rate. Then, as a cataract begins to coalesce, the lens is bumped off the age ramp, and the 420/360 FL metric may fall significantly.

Figure 8:
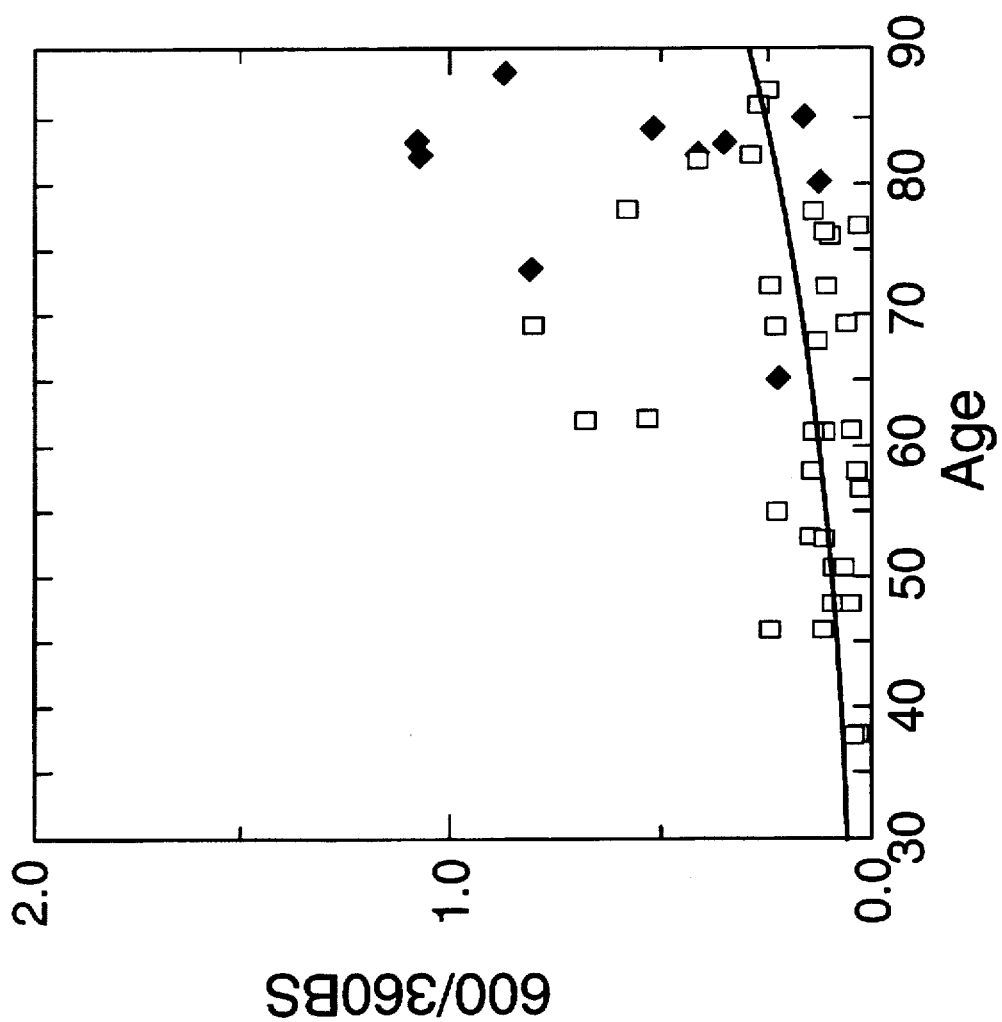
FIG. 8 shows the ratio of the backscatter peak intensity induced by 600-nm excitation as a function of age. This Figure includes the same population of normal (open symbols) and cataractous (solid symbols) lenses set forth in FIG. 8 hereof.

The 600/360 backscattering ratio plotted as a function of age (for the same population of lenses used to generate FIG. 7) is seen in FIG. 8 (hollow data points). In general, there is an increasing trend with age, but the deviations from the prevailing trend are more severe than when examining fluorescence ratios. Scattering metrics may be more sensitive indicators of the overall optical health of the lens, but their more erratic behavior may be difficult to interpret. Plots of green and blue backscattering ratios (e.g., 500/360 and 420/360) for the same data set show very similar distributions to those seen in FIG. 8. It was found that the scattering of shorter visible wavelengths in young lenses starts at higher absolute values, the rate of increase in scattering with aging is comparable for all visible wavelengths. The behavior (enhanced scattering) of cataractous versus noncataractous lenses is also similar to that of FIG. 8 when shorter visible wavelengths are considered.

It is helpful, in terms of diagnosing progress towards cataract formation or progress of other disease processes which affect the lens, to have metrics which move both in the direction of more rapidly accelerating optical aging (such as the backscattering ratio of FIG. 8) and in the opposite direction (as with the fluorescence ratio of FIG. 7). By examining a combination of such metrics, it should be possible to derive earlier warning indicators of eventual cataract formation or other degenerative processes. Similarly, by using a combination of indicators, it may be possible to distinguish those lenses which are just signaling accelerated optical aging due to either endogenous or exogenous factors from those where coalescence of a cataract or some other degenerative process has already begun.

In summary, the method of the present invention is readily adaptable to in vivo optical characterization of the human lens with minor adaptation of the fiber probe as described above. The backscatter/fluorescence spectra for the specified exciting wavelengths can each be collected in a fraction of a second at excitation levels which are both safe and too weak to elicit flashblindness or other aversion responses in the alert subject. The designated sequence of excitation wavelengths and the timing of the exposures is easily programmed and can be changed as required. The quantitative optical measurements on the lens can be successfully accomplished in situ despite the presence of the intervening ocular media and the potential interference from, for example, corneal autofluorescence. The delivery/collection fiber array can be embedded in a flat-faced contact lens and held in place for the duration of the measurements (a few seconds). The fiber tip can effectively be placed in contact with the ocular fluid trapped under the contact lens to avoid an air-fluid interface (as this would generate an undesirable reflection).

The three-dimensional profiles cast from the spectral sequences, such as shown in FIGS. 2 and 3, provide a comprehensive optical signature which can be analyzed to gauge the overall optical health of the lens. However, it may not be necessary or desirable to generate the entire sequence of curves. A more limited sequence of exposures, perhaps avoiding the shorter uv wavelengths ($\leq$350-nm) altogether may suffice to generate a useful combination of optical metrics which may include the fluorescence and backscatter ratios and the WL-BS curves, such as depicted in FIGS. 7 and 8, and 4-6, respectively.

The foregoing description of the invention has been presented for purposes of illustration and description and is not intended to be exhaustive or to limit the invention to the precise form disclosed, and obviously many modifications and variations are possible in light of the above teaching.

The embodiments were chosen and described in order to best explain the principles of the invention and its practical application to thereby enable others skilled in the art to best utilize the invention in various embodiments and with various modifications as are suited to the particular use contemplated. It is intended that the scope of the invention be defined by the claims appended hereto.

What is claimed is:

1. An in vivo method for determining the optical quality of human ocular lenses, said method comprising the steps of:
   a. illuminating the lens under investigation with a predetermined wavelength of electromagnetic exciting radiation;
   b. measuring the intensity of the exciting radiation;
   c. collecting backscattered and fluorescent radiation from the lens excited thereby; and
   d. normalizing the collected backscattered and fluorescent radiation to the measured intensity of the exciting radiation.

2. The method as described in claim 1, further comprising the step of sweeping the illuminating wavelengths of electromagnetic radiation through a predetermined range of wavelengths.

3. The method as described in claim 1, further comprising the step of comparing the collected backscattered and fluorescent radiation with a data set of similar measurements obtained from a reference set of normal human lenses having various ages; whereby the optical quality of the lens under investigation can be determined relative thereto.

4. The method as described in claim 2, wherein the predetermined range of wavelengths is between 300- and 600-nm.

5. The method as described in claim 4, wherein the bandwidth of the excitation radiation is approximately 10-nm.

6. The method as described in claim 1, wherein the exciting radiation in said step of illuminating the lens under investigation is delivered to the lens using at least one optical fiber.

7. The method as described in claim 1, wherein the backscattered and fluorescent radiation received from the excited lens under investigation in said collecting step is collected using at least one optical fiber.

* * * * *